(12) United States Patent
Karlsen et al.

(10) Patent No.: US 8,864,718 B2
(45) Date of Patent: Oct. 21, 2014

(54) AUTO INJECTOR WITH AUTOMATIC NEEDLE SHIELDING

(75) Inventors: Morten Friis Karlsen, København N. (DK); Jens Andersen Gad, Hellerup (DK); Bjørn Knud Andersen, Struer (DK)

(73) Assignee: Bang & Olufsen Medicom A/S, Struer (DK)

( * ) Notice: Subject to any disclaimer, the term of this patent is extended or adjusted under 35 U.S.C. 154(b) by 360 days.

(21) Appl. No.: 13/503,333

(22) PCT Filed: Oct. 25, 2010

(86) PCT No.: PCT/EP2010/066072
§ 371 (c)(1),
(2), (4) Date: Aug. 17, 2012

(87) PCT Pub. No.: WO2011/048223
PCT Pub. Date: Apr. 28, 2011

(65) Prior Publication Data
US 2012/0323186 A1 Dec. 20, 2012

(30) Foreign Application Priority Data
Oct. 23, 2009 (EP) ..................................... 09173966

(51) Int. Cl.
*A61M 5/32* (2006.01)
*A61M 5/34* (2006.01)
*A61M 5/20* (2006.01)

(52) U.S. Cl.
CPC .................. *A61M 5/326* (2013.01); *A61M 5/20* (2013.01); *A61M 2005/208* (2013.01); *A61M 5/2066* (2013.01); *A61M 5/2033* (2013.01); *A61M 2005/3247* (2013.01); *A61M 5/3202* (2013.01); *A61M 2005/206* (2013.01); *A61M 5/347* (2013.01)

USPC ............................ 604/192; 604/197; 604/198

(58) Field of Classification Search
USPC .......................................... 604/192, 197–198
See application file for complete search history.

(56) References Cited

U.S. PATENT DOCUMENTS

| 4,874,383 A | 10/1989 | McNaughton |
| 5,106,379 A | 4/1992 | Leap |

(Continued)

FOREIGN PATENT DOCUMENTS

| CN | 1819852 A | 8/2006 |
| CN | 1921899 A | 2/2007 |

(Continued)

OTHER PUBLICATIONS

International Search Report and Written Opinion received for PCT Patent Application No. PCT/EP2010/066072, mailed on Feb. 24, 2011, 12 pages.

(Continued)

*Primary Examiner* — Kevin C Sirmons
*Assistant Examiner* — Deanna K Hall
(74) *Attorney, Agent, or Firm* — Morrison & Foerster LLP

(57) ABSTRACT

The present invention relates to an auto injector, e.g. a disposable auto injector, that can be safely operated for automatic injection of a dose of medication by the recipient of the medication, having a housing for accommodation of a container with at least one compartment for accommodation of a medicament to be injected and a needle mounting site for user mounting of a needle covered by a needle cap before injection, and a needle shield that is accommodated in the housing in a retracted position before mounting of the needle and that is configured to be automatically moved forward to a protruded position by a needle shield driver upon mounting of the needle and removal of the needle cap.

14 Claims, 16 Drawing Sheets

(56) References Cited

U.S. PATENT DOCUMENTS

| | | |
|---|---|---|
| 5,366,447 A | 11/1994 | Gurley |
| 2005/0113750 A1 | 5/2005 | Targell |
| 2007/0100290 A1 | 5/2007 | Schiffmann et al. |
| 2007/0197968 A1 | 8/2007 | Pongpairochana et al. |

FOREIGN PATENT DOCUMENTS

| | | |
|---|---|---|
| CN | 101454032 A | 6/2009 |
| EP | 1518575 A1 | 3/2005 |
| WO | 2004/028598 A1 | 4/2004 |
| WO | 2005/044345 A1 | 5/2005 |
| WO | 20051077441 A2 | 8/2005 |
| WO | 2006/080893 A1 | 8/2006 |
| WO | 2008/031235 A1 | 3/2008 |
| WO | 2008/087071 A1 | 7/2008 |
| WO | 2009/063030 A1 | 5/2009 |

OTHER PUBLICATIONS

Office Action received for Chinese Patent Application No. 201080057073.4, issued on Aug. 1, 2013, 19 pages (10 pages of English Translation and 9 pages).

(a)      (b)      (c)      (d)

AUTO INJECTOR WITH AUTOMATIC NEEDLE SHIELDING

CROSS REFERENCE TO RELATED APPLICATIONS

This is a U.S. National Phase patent application of PCT/EP2010/066072, filed Oct. 25, 2010, which claims priority to the European Patent Application No. 09173966.4, filed Oct. 23, 2009, each of which is hereby incorporated by reference in the present disclosure in its entirety.

The present invention relates to an injector that can be safely operated for automatic injection of a dose of medication by the recipient of the medication. The auto injector may be disposable.

Auto injectors are well-known in the art. Auto injectors have been provided with varying degrees of automatic function, ranging from only automatic penetration or only automatic injection to fully automatic function including penetration, injection, withdrawal, and shielding of the needle.

Some auto injectors are used to deliver so-called ready-to-use medicament to the patient packaged in cartridges, ampoules or syringes in liquid state that can be stored for a long time before use.

Other medicaments have to be mixed with liquid shortly before injection because of degradation and loss of effect of the medicament quickly after mixing with liquid.

WO 2006/080893 A1 discloses an auto injector with a needle shield. A needle with an outer needle cover and an inner needle cover is mounted to the auto injector before injection. The outer needle cover is removed by hand. A separate tool is provided for removal of the inner needle cover and for releasing the needle shield and bringing it forward.

WO 2004/028598 A1 discloses an auto injector with a needle shield. The injector is received by the patient with the needle shield in a retracted position held there by appropriate releasable holding means. A mode selector is positioned with protrusions in an unlocked position. This facilitates for the patient to attach a needle by threading a needle, arranged inside a needle cover, onto the threaded neck portion of the container holding housing. An inner end of the needle will thereby penetrate a membrane at the front end of the container, thereby establishing a passage between the needle and the interior of the container. It is also conceivable to omit the releasable holding means whereby the device is delivered with an extended needle shield. When the mode selector is placed in the unlocked position, the needle shield can be pushed inside the main housing because of the configuration of grooves enabling protrusions to slide between a front and a rear position in the groove. In this case the needle shield is pushed inside when a needle is attached. The mode selector is then turned and pushed forward to a locked position, whereby a dose actuating sleeve is turned and moved forward by a spring acting on the dose actuating sleeve which in turn moves the needle shield forward. The protrusions of the dose actuating sleeve are moved in the grooves to a position wherein protrusions engage with mating ledges on the inner surface of the main housing, thereby locking the needle shield. This movement causes the needle cover to be pushed off the needle and the needle shield surrounds the needle in a locked position.

It is an object of the present invention to provide an auto injector of the type that requires user mounting of the needle before injection, with a further automated and user-friendly medicament delivery sequence and that is easy to manufacture.

According to the present invention the above-mentioned and other objects are fulfilled by provision of an auto injector with a housing for accommodation of a container with at least one compartment for accommodation of a medicament to be injected and a needle mounting site for user mounting of a needle covered by a needle cap before injection.

The auto injector further has a needle shield that is accommodated in the housing and that is movable along a longitudinal axis of the housing with relation to a fixed part of the housing, and a needle shield driver that is anchored to the fixed part of the housing and connected to the needle shield for displacing the needle shield along the longitudinal axis of the housing with relation to the fixed part of the housing.

Before mounting of the needle, the needle shield is kept in a retracted position by a locking mechanism. The locking mechanism is released during mounting of the needle with the needle cap to the needle mounting site, whereby the needle shield driver, upon release of the locking mechanism, displaces the needle shield from its retracted and locked position to a first protruded position in which the needle shield prevents inadvertent user contact with the needle.

Preferably, the needle shield driver displaces the needle shield concurrently with user removal of the needle cap from the needle. For example, the needle cap may abut the end of the needle shield during removal of the needle cap, so that the needle shield and the needle cap moves forward together in abutment. In this way, the needle remains unexposed to the surroundings during mounting of the needle and subsequent removal of the needle cap.

The needle may be mounted to the needle mounting site with a bayonet lock, a thread, or the like.

The needle mounting site may be accommodated in the housing in a retracted and inaccessible position before mounting of the needle and the needle mounting site may further be configured to be moved forward to an accessible position for mounting of the needle by a mounting site driver upon user actuation of the auto injector. The user actuation may be constituted by pressing a button or turning a knob, etc.

The auto injector may be prevented from further operation until proper mounting of the needle.

The container with the needle may be movably positioned in the housing by an injection driver between a first position in which position the needle is covered by the needle shield in the protruded position and a second position in which position the needle protrudes beyond the needle shield. Further, the auto injector may comprise a first injection lock configured in a locked state for preventing container movement from the first position to the second position, and an injection trigger member configured for releasing the first injection lock to an unlocked state by user operation of the injection trigger member in which unlocked state the first injection lock does not prevent the injection driver from moving the container from the first position to the second position.

The auto injector may further comprise a second injection lock configured in a locked state for preventing container movement from the first position to the second position by user operation of the injection trigger member and wherein the needle shield is configured for releasing the second injection lock to an unlocked state by pressing the needle shield against the injection site in which unlocked state the second injection lock does not prevent container movement from the first position to the second position by user operation of the injection trigger member. When the needle shield is pressed against the injection site, it is allowed to move a certain distance into the housing thereby releasing the second injection lock. The needle shield is still locked in the protruded position in the sense that it cannot move further into the housing and when pressed against the injection site, the needle is still accommodated behind the needle shield out of contact with the injection site until injection is commenced by user actuation.

Preferably, the second injection lock has to be released before release of the first injection lock in order to start injection whereby injection cannot be started by the user first releasing the first injection lock and subsequently pressing the needle shield against the injection site.

The auto injector may further be configured so that release of the injection trigger member after commencement of injection and before completion of the injection causes medicament injection to stop, and subsequent actuation of the injection trigger member causes medicament injection to be resumed.

The auto injector may further be configured so that release of the needle shield after commencement of injection and before completion of the injection causes medicament injection to stop, and subsequent pressing the needle shield against the injection site causes medicament injection to be resumed.

The auto injector may further be configured so that the container with the needle is automatically retracted upon completion of medicament injection and upon the user removing the needle shield from contact with the injection site so that the needle is accommodated behind the needle shield after delivery of the medicament thereby preventing inadvertent user contact with the needle. Thus, the auto injector may further comprise a retraction lock for prevention of retraction of the container by a retraction driver in a locked state. Further, the needle shield may be configured for releasing the retraction lock to an unlocked state when the user removes the needle shield from the injection site upon completion of the injection thereby allowing the retraction driver to retract the container to a retracted position wherein the needle is covered by the needle shield thereby preventing inadvertent user contact with the needle upon completion of injection.

The auto injector may further be configured so that the needle shield is automatically moved forward to a further protruded position by the needle shield driver when the user removes the needle shield from the injection site upon completion of the injection so that the needle is covered by the needle shield thereby preventing inadvertent user contact with the needle upon completion of injection.

Each of the drivers may be an electro-mechanical driver, e.g. comprising an electromotor, a piezoelectric transducer, etc, a pneumatic driver, a hydraulic driver, a mechanical driver, such as a spring, such as a coil spring, a constant force spring, etc, etc.

The locking mechanism may for example comprise an L-shaped slot provided in a wall in the housing, e.g. an internal wall in the housing. The housing of the auto injector may for example accommodate a container housing for accommodation of the container, and the L-shaped slot may be provided in a wall of the container housing, The locking mechanism may then further comprise a first protrusion of the needle shield that is movably accommodated in the slot and wherein the L-shaped slot has an orientation that prevents movement of the needle shield with the first protrusion along the longitudinal axis of the housing before mounting of the needle.

The locking mechanism may be released when the wall is turned with the needle cap during mounting of the needle, for example by abutment of the wall and the needle cap, whereby the first protrusion is moved in the L-shaped slot to a position where the L-shaped slot changes direction and allows the needle shield with the first protrusion to be displaced along the longitudinal axis of the auto injector by the force of the needle shield driver.

Alternatively, the L-shaped slot may be provided in the needle shield and a first protrusion may be provided in a wall in the housing that is movably accommodated in the slot and wherein the L-shaped slot has an orientation that prevents movement of the needle shield with relation to the first protrusion along the longitudinal axis of the housing before mounting of the needle. The locking mechanism may be released when the needle shield is turned with the needle cap during mounting of the needle, for example by abutment of the needle shield and the needle cap, whereby the first protrusion is moved in the L-shaped slot to a position where the L-shaped slot changes direction and allows the needle shield to be displaced with relation to the first protrusion along the longitudinal axis of the auto injector by the force of the needle shield driver.

The locking mechanism may comprise a needle shield locking arm of the housing, having a protrusion that engages and holds a proximate end of the needle shield at the needle mounting site thereby keeping the needle shield of the auto injector in the retracted position before mounting of the needle. The locking mechanism may be released by a protrusion of the needle cap displacing the protrusion of the needle shield locking arm out of engagement with the needle shield during mounting of the needle thereby allowing the needle shield to be displaced with relation to the fixed part of the housing along the longitudinal axis of the auto injector by the force of the needle shield driver.

A mechanical stop may further be provided in the housing of the auto injector that defines a retracted position of the needle shield when the needle shield is pressed against an injection site. In the retracted position, the needle shield prevents the needle from contacting the injection site. In the retracted position, the needle shield may further establish a connection between the injection trigger member provided in the housing and the first injection lock in such a way that pressing the injection trigger member releases the first injection lock allowing the injection driver to displace the container together with the needle from its current first position, in which position the needle is accommodated behind the needle shield, to a second position, in which position the needle protrudes beyond the needle shield for penetration of tissue at the injection site.

The needle shield may have a second protrusion that is resiliently connected to the needle shield and configured to slide along an internal surface of the housing when the needle shield is displaced along the longitudinal axis of the auto injector. The second protrusion is urged into abutting contact with the surface by the spring force of the resilient connection to the needle shield.

A groove may be provided in the internal surface of the housing, with a longitudinal direction that is parallel to the longitudinal axis of the housing. The groove accommodates the second protrusion urged into the groove by the spring force of the resilient interconnection with the needle shield when the needle shield is in the first protruded position.

The groove has a distal end defined by an end wall of the groove that may function as a mechanical stop so that rearward movement of the needle shield, e.g., caused by pressing the needle shield against the injection site, is stopped by abutment of the second protrusion and the distal end of the groove.

A tapered protrusion may further be provided in the groove that is tapered in the forward moving direction of the needle shield and thereby allows passage of the second protrusion in the forward moving direction of the needle shield. In the rearward moving direction of the needle shield the protrusion in the groove exhibits a wall protruding from the groove in a direction substantially perpendicular to the longitudinal axis of the housing thereby preventing passage of the second protrusion in the rearward moving direction of the needle shield. Thus, the tapered protrusion in the groove allows the needle shield to move from the first protruded position to a second protruded position upon removal of the auto injector from the injection site after completion of an injection and prevents subsequent retraction of the needle shield from the second protruded position by abutment of the second protrusion of the needle shield and the perpendicular wall of the protrusion in the groove so that the needle remains protected and covered by the needle shield after injection.

Alternatively, a movable member may be provided in the groove that defines the first protruded position of the needle shield by abutment of the second protrusion of the needle shield and the movable member. Upon removal of the auto injector from the injection site after completion of an injection, the movable member is displaced out of abutment with the second protrusion thereby allowing passage in the groove of the second protrusion in the forward moving direction of the needle shield so that the needle shield is allowed to move to the second protruded position. The movable member is returned to its protruding position in the groove upon passage of the second protrusion in the forward moving direction of the needle shield and thereby prevents passage of the second protrusion in the rearward moving direction of the needle shield so that subsequent retraction of the needle shield from the second position is prevented by abutment of the second protrusion of the needle shield and the movable member so that the needle remains protected and covered by the needle shield after injection.

The above and other features and advantages of the present invention will become readily apparent to those skilled in the art by the following detailed description of exemplary embodiments thereof with reference to the attached drawings, in which:

FIG. 1 shows an auto injector as claimed from two different angles,

FIG. 2 shows the auto injector of FIG. 1 in a state ready for mounting of the needle, FIG. 3 shows mounting of the needle, and appearance of the needle shield, FIG. 4 schematically illustrates cooperating parts of an auto injector with an automatic needle shield as claimed, FIG. 5 schematically illustrates various operational steps of the auto injector of FIG. 4, FIG. 6 shows an auto injector with an automatic needle shield in various states, FIG. 7 shows an auto injector before needle mounting in perspective with cut-outs allowing internal parts to be visible, FIG. 8 shows the auto injector of FIG. 7 after needle mounting, FIG. 9 shows the auto injector of FIGS. 7 and 8 in exploded and perspective view, FIG. 10 shows the container housing in perspective, FIG. 11 shows the needle shield in perspective, FIG. 12 schematically illustrates cooperating parts of another auto injector with an automatic needle shield, FIG. 13 schematically illustrates various operational steps of the auto injector of FIG. 12, FIG. 14 schematically illustrates cooperating parts of an auto injector with an automatic needle shield as claimed, FIG. 15 schematically illustrates a needle shield with a bayonet coupling to the housing, and FIG. 16 schematically illustrates parts of an injection mechanism.

The figures are schematic and simplified for clarity, and they merely show details, which are essential to the understanding of the invention, while other details have been left out. Throughout, the same reference numerals are used for identical or corresponding parts.

It should be noted that in addition to the exemplary embodiments of the invention shown in the accompanying drawings, the invention may be embodied in different forms and should not be construed as limited to the embodiments set forth herein. Rather, these embodiments are provided so that this disclosure will be thorough and complete, and will fully convey the concept of the invention to those skilled in the art.

FIG. 1 shows an example of an auto injector 10 as defined in the appended set of claims. The illustrated auto injector 10 has an elongated cylindrical housing 12 with a proximate end 14 with the needle mounting site 16 shown in its retracted position. A cylindrical turning knob 18 is located at the opposite distal end 20 of the housing 12, and an injection trigger member 22 protrudes from and is integer with the turning knob 18. The housing 12 has a substantially circular cross-section for an easy grip by hand. The illustrated auto injector 10 has a length of 15 cm and a diameter of 3 cm. For reasons of user comfort, it is advantageous that the housing does not have an exact circular cross-section in order to prevent the device from rolling, e.g. on top of a table. In the illustrated auto injector 10, the off-centered turning knob 18 deviates from the otherwise circular cross-section of the housing 12. Further, the housing has a ridge 23 extending along the longitudinal axis of the housing 12 for alignment with the trigger member 22 on the turning knob 18 in one of its angular positions during use.

The illustrated auto injector 10 also has a window 24 so that the user can watch the mixing process as explained further below.

FIG. 2 shows the auto injector of FIG. 1 with the needle mounting site 16 in its protruded position ready for user mounting of the needle. In the auto injector 10 shown in FIG. 1, rotation of the turning knob 18 from its initial position to its start position of the medicament delivery sequence causes the needle mounting site 16 to move to its protruded position.

Another auto injector may be provided in which mixing of the medicament is performed prior to mounting of the needle. In such an auto injector, turning of the knob may initiate the mixing process and subsequently cause the needle mounting site 16 to move into its protruded position.

The needle mounting site 16 of the illustrated auto injector 10 comprises a cylindrical threaded member 30 with a central aperture covered by a seal 32. The auto injector 10 is now ready for mounting of the needle 26. In the example shown in FIG. 3, the needle 26 is covered by a needle cap 28. The needle 26 is further connected to a threaded cylindrical member (not visible) and extends through a centre of the threaded cylindrical member. The needle cap 28 is releasably attached to the threaded cylindrical member. During mounting of the needle 26, the threaded cylindrical member (not visible) carrying the needle (not visible) is screwed onto the mating threaded member 30 of the needle mounting site 16 by the user gripping the needle cap 28. During the mounting operation, the needle 26 penetrates the seal 32 so that medicament in the auto injector may be delivered to the injection site through the needle 26.

FIG. 4 schematically illustrates one locking mechanism for the needle shield 38 wherein the needle shield 38 is coupled to a part of the housing 12, in the illustrated example the container housing 46, of the auto injector 10 with a locking mechanism like a bayonet lock. The locking mechanism prevents forward movement of the needle shield 38 in the direction towards the proximate end 14 of the auto injector 10 counteracting the force applied to the needle shield 38 by a needle shield driver 42 (not shown) that moves the needle shield 38 forward upon release of the locking mechanism. The locking mechanism comprises an L-shaped slot 25 provided in the container housing 46 and a protrusion 56 of the needle shield 38 that cooperates with the slot 25. The protrusion 56 of the needle shield 38 fits in the slot 25 and engages with the slot 25 so that the slot 25 functions as a guiding rail for the protrusion 56. A short leg of the L-shaped part of the slot 25 spans circumferentially in the container housing 46 in a plane perpendicular to the longitudinal direction of the housing 12, and a long leg of the L-shaped part of the slot 25 spans in parallel with the longitudinal direction of the housing 12. In the retracted position of the needle shield 38 shown in FIG. 4, the protrusion 56 resides at the end of the slot 25 at the end of the short leg of the L-shaped slot 25 in which position, the protrusion 56 in cooperation with the slot 25 prevents forward movement of the needle shield 38 from its retracted position. The needle shield 38 is in a locked retracted position wherein the needle mounting site 16 is exposed to the surroundings for easy access during needle mounting.

The needle shield 38 further has a protrusion 58 that is resiliently connected to the needle shield 38 for cooperation with grooves 60 in the housing 12 for prevention of retraction of the needle shield 38 subsequent to forward movement of the needle shield 38 as will be further explained below.

When the needle 26 with the needle cap 28 is screwed onto the needle mounting site 16; during the final turn, the needle cap 28 engages with the container housing 46 through the needle mounting site and turns the container housing 46 a predetermined angle around the longitudinal axis of the housing 12, for example 45°, so that the protrusion 56 is moved to the opposite end of the short leg of the L-shaped slot 25 (by relative movement) and thereby to the start of the long leg of the L-shaped slot 25 whereby the needle shield 38 is released and allowed to move to its protruded position by the force applied by the needle shield driver (not shown). The slot 25 may be angled with relation to the longitudinal axis of the housing 12 so that the needle shield 38 is turned during part of the movement from the retracted position to the protruded position for re-alignment of other features of the needle shield, for example the distance piece explained below, with corresponding features in the housing facilitating subsequent operation of the auto injector 10.

Various positions of the needle shield 38 are shown in FIG. 5 for illustration of various operational steps of the auto injector 10 in sequence from top to bottom of FIG. 5.

FIG. 5(a) shows the auto injector 10 before mounting of the needle as in FIG. 4.

In FIG. 5(b), the needle 26 has been mounted and the final turn of the needle cap 28 with the needle 26 has been performed whereby the needle shield 38 has been turned so that the protrusion 56 is now engaged with the long leg of the L-shaped slot 25 and is moved forward towards its protruded position by the needle shield driver 42, e.g. a coil spring, concurrently with user removal of the needle cap 28 from the needle 26. During removal of the needle cap 28, the needle cap 28 abuts the end of the needle shield 38 so that the needle shield 38 and the needle cap 28 moves forward in abutment whereby the needle 26 remains unexposed to the surroundings during mounting of the needle 26 and subsequent removal of the needle cap 28.

In FIG. 5(c), the needle shield 38 is in its first protruded position and the auto injector 10 is ready for injection. In the first protruded position, the protrusion 56 rests against the proximate end of the slot 25. During forward movement of the needle shield 38, the protrusion 58 that is resiliently connected to the needle shield 38 slides along an internal wall of the housing 12 and is urged into the groove 60 in the wall by the spring force of the resilient interconnection with the needle shield 38.

In FIG. 5(d), the needle shield 38 is pressed against the injection site and injection is performed. The groove 60 cooperates with the protrusion 58 and has an end 62 that functions as a mechanical stop so that rearward movement of the needle shield 38 caused by pressing the needle shield against the injection site is stopped by abutment of the protrusion 58 and the end 62, whereby the injection site is not brought into contact with the needle 26 before user actuation of the auto injector 10 for injection. As illustrated in FIG. 5(c), the needle shield 38 is displaced rearward when the needle shield 38 is pressed against the injection site, whereby other features of the auto injector 10 are brought into relative positions that allow the user to trigger forward movement of the container housing 46 with the container 50 with the needle 26 for penetration of the injection site and injection of the medicament in the container compartment(s).

In FIG. 5(e), injection has been completed and the user has removed the auto injector 10 from the injection site. The forward movement of the container housing 46 has also moved the proximate end 66 of the slot 25 forward so that the needle shield driver 42 is allowed to automatically move the needle shield 38 to its second protruded position upon removal of the auto injector 10 from the injection site. In its second protruded position, the needle shield 38 is fully protruded and locked by the tapered stop 64 provided in the groove 60. The tapered stop 64 allows forward movement of the needle shield 38 but prevents subsequent retraction of the needle shield 38 so that the needle 26 remains protected and covered by the needle shield after injection so that the auto injector 10 may be disposed safely, and further user contact with the needle 26 is prevented.

The various positions of the needle shield 38 are also shown non-schematically in FIG. 6. FIG. 6(a) shows the auto injector 10 before mounting of the needle as in FIGS. 4 and 5(a). FIG. 6(b) shows the auto injector 10 with the needle 26 mounted immediately before the final turn of the needle cap 28 is performed. In FIG. 6(c), the needle cap 28 has been removed and the needle shield 38 is in its first protruded position ready for use at the injection site. FIG. 6(d) shows the auto injector 10 after injection and removal of the auto injector 10 from the injection site and thus, the needle shield 38 is in its second protruded position. The second protruded position of the needle shield 38 is a locked position wherein rearward movement of the needle shield 38 is not possible.

FIG. 7 shows the auto injector 10 of FIGS. 5-7 in perspective and with the upper half of its parts cut away so that internal parts of the auto injector are visible. The auto injector is in the same state as in FIG. 4 and FIG. 5(a), i.e. before mounting of the needle with the needle shield 38 in its retracted position in which the needle mounting site 16 is exposed for easy access. The protrusion 56 of the needle shield 38 is accommodated in the short leg of the slot 25 so that forward movement of the needle shield 38 by the force applied to the needle shield by the coil spring 42 is prevented.

FIG. 8 shows the auto injector 10 of FIG. 7 upon mounting of the needle 26 with the needle shield 38 in its first protruded position shielding the needle 26 from inadvertent contact with the user as also shown in FIG. 5(c). The needle shield 38 has been turned during needle mounting whereby the protrusion 56 has been moved from the position shown in FIG. 7 in the short leg of the L-shaped slot 25 to the opposite end of the short leg of the L-shaped slot 25 thereby entering the long leg of the L-shaped slot 25 so that the needle shield 38 with the protrusion 56 is allowed to move forward to the first protruded position wherein the protrusion 56 rests against the proximate en 66 of the slot 25.

Figure 11:
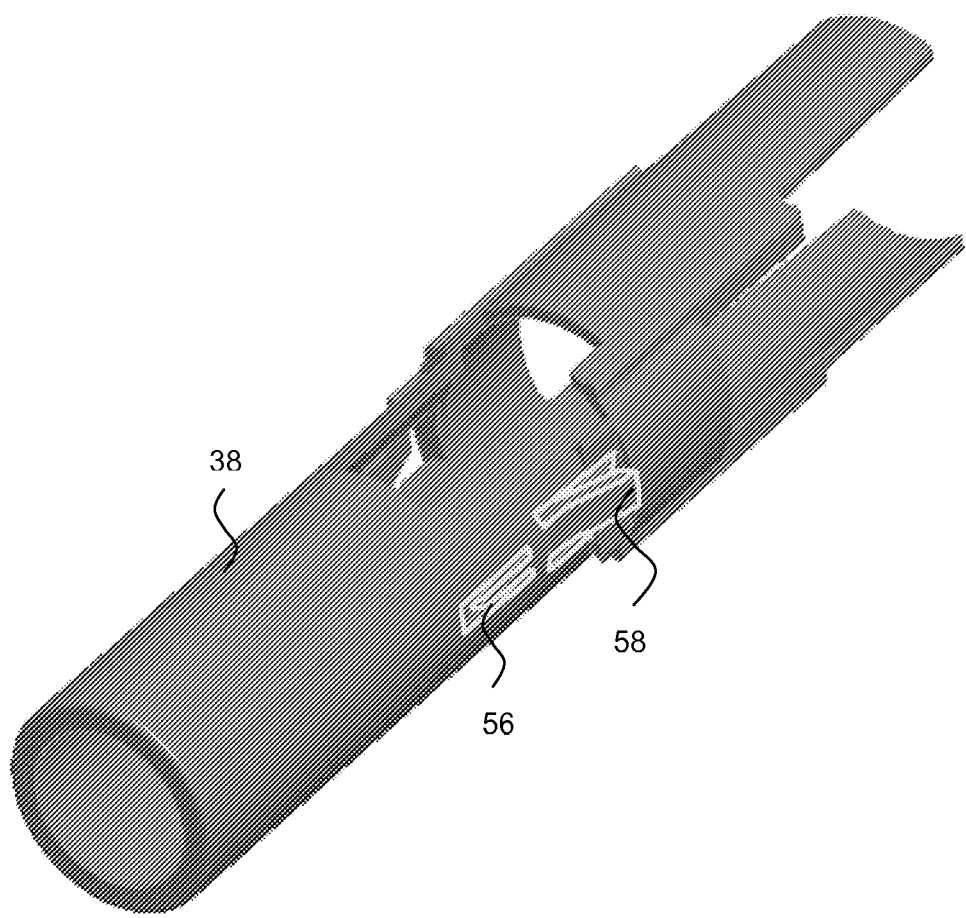

FIG. 11 shows the needle shield 38 in more detail with the protrusion 56 cooperating with the slot 25 of the container housing 46 and the protrusion 58 that is resiliently connected with the needle shield 38 and cooperates with the groove 60 in a wall of the housing 12.

Figure 1:
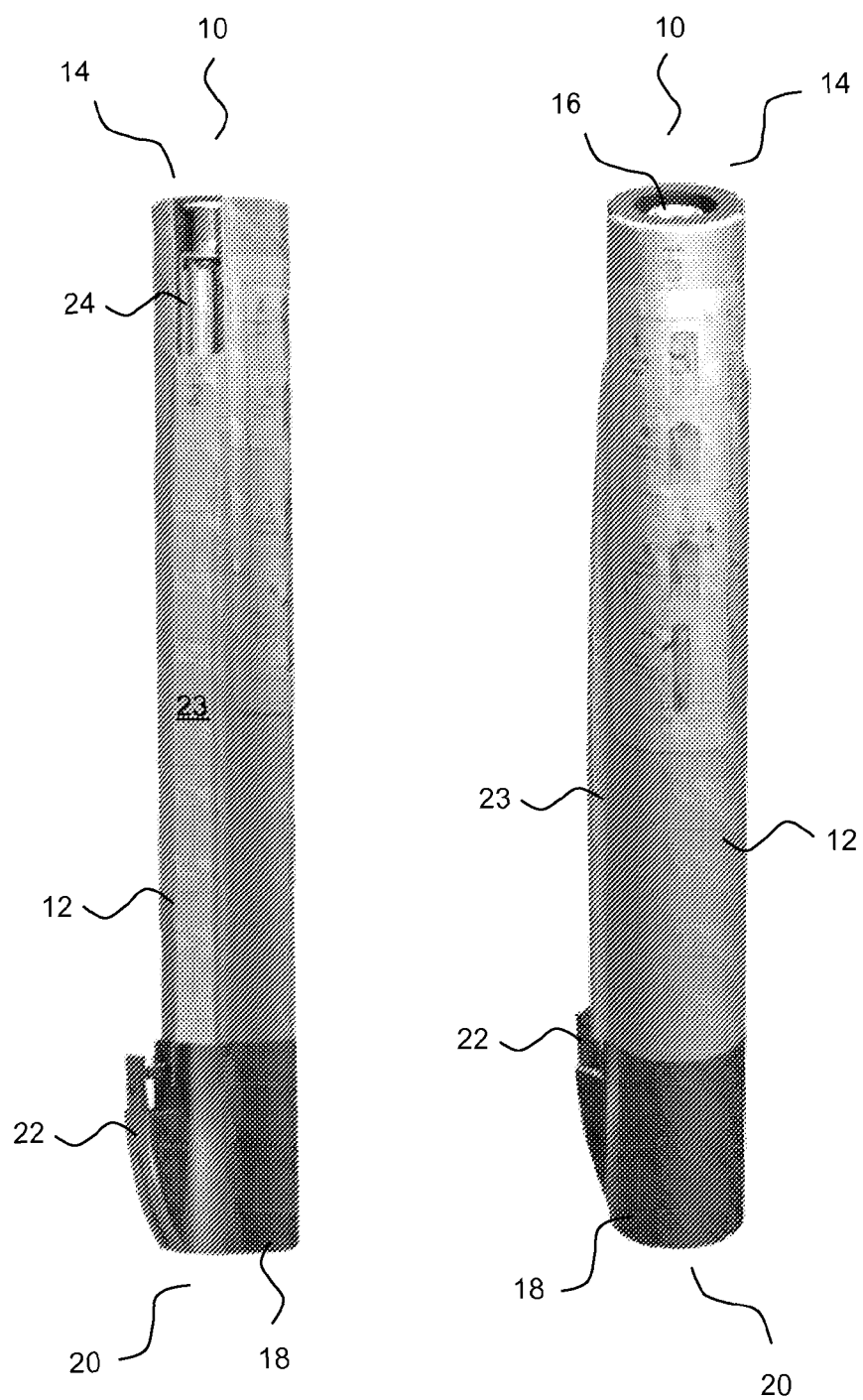
Figure 2:
Figure 3:
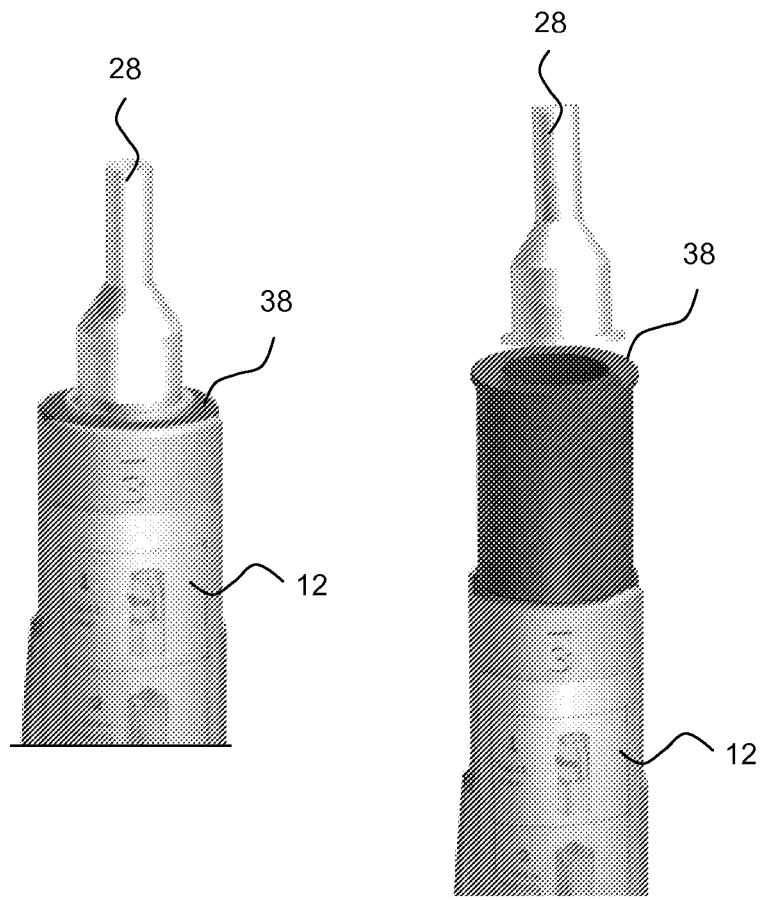
Figure 4:
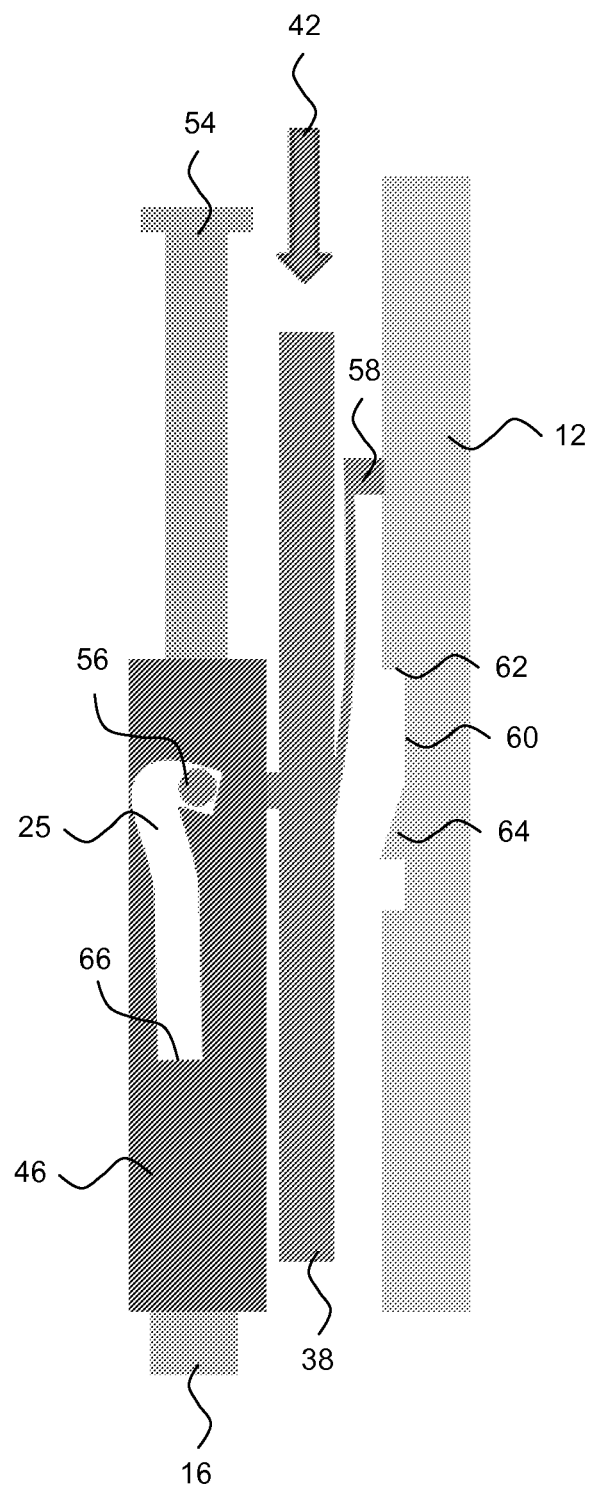
Figure 5:
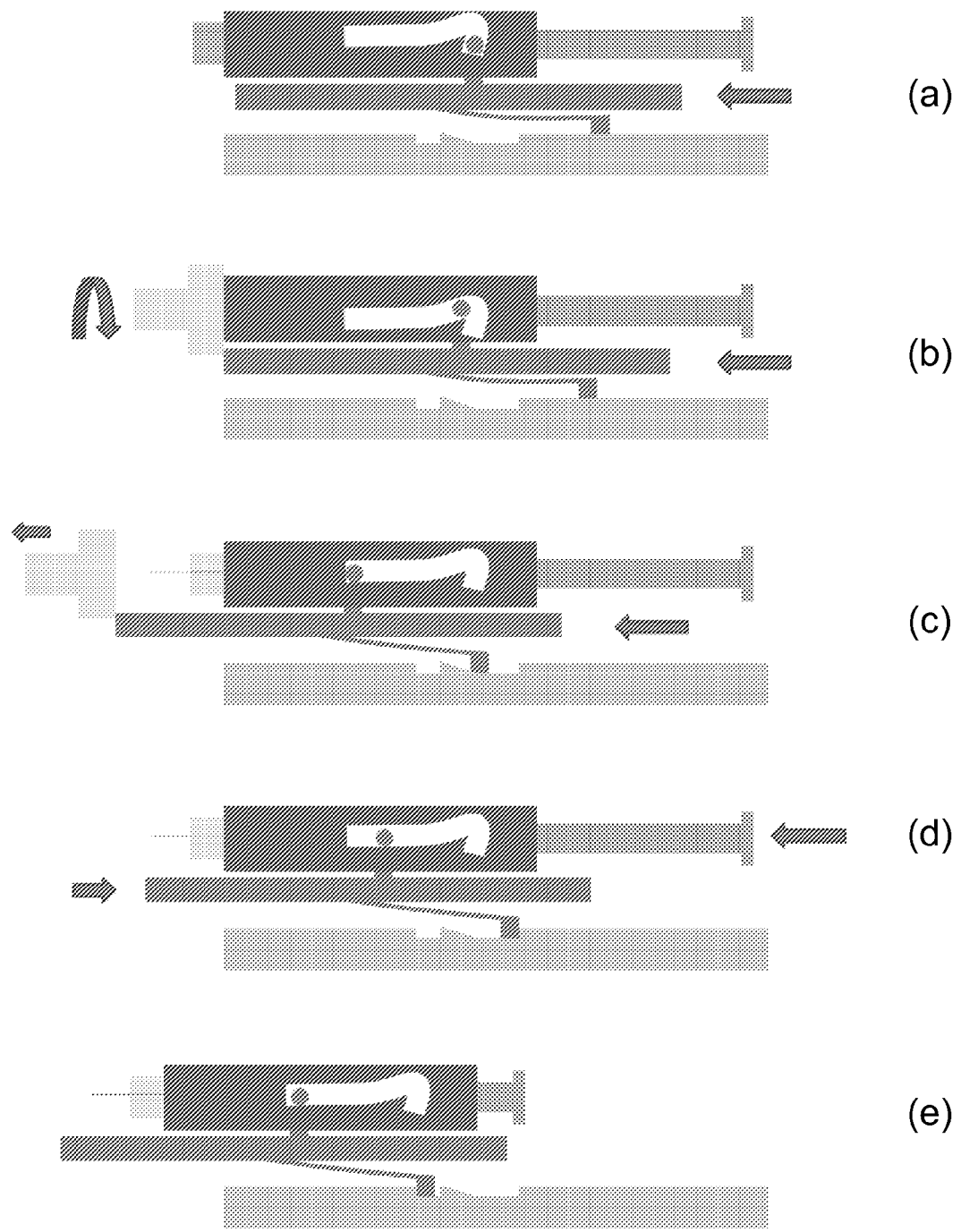
Figure 6:
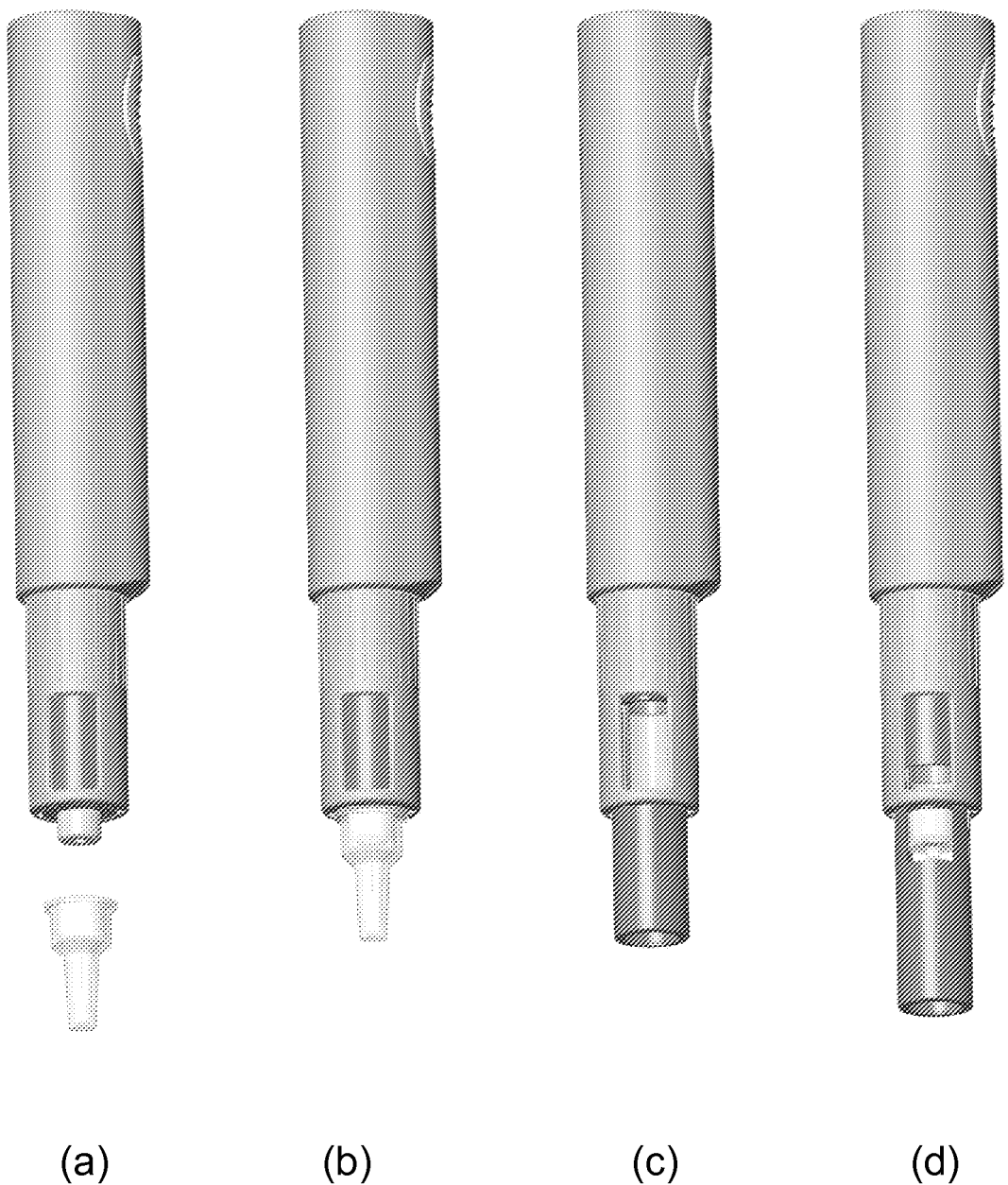
Figure 7:
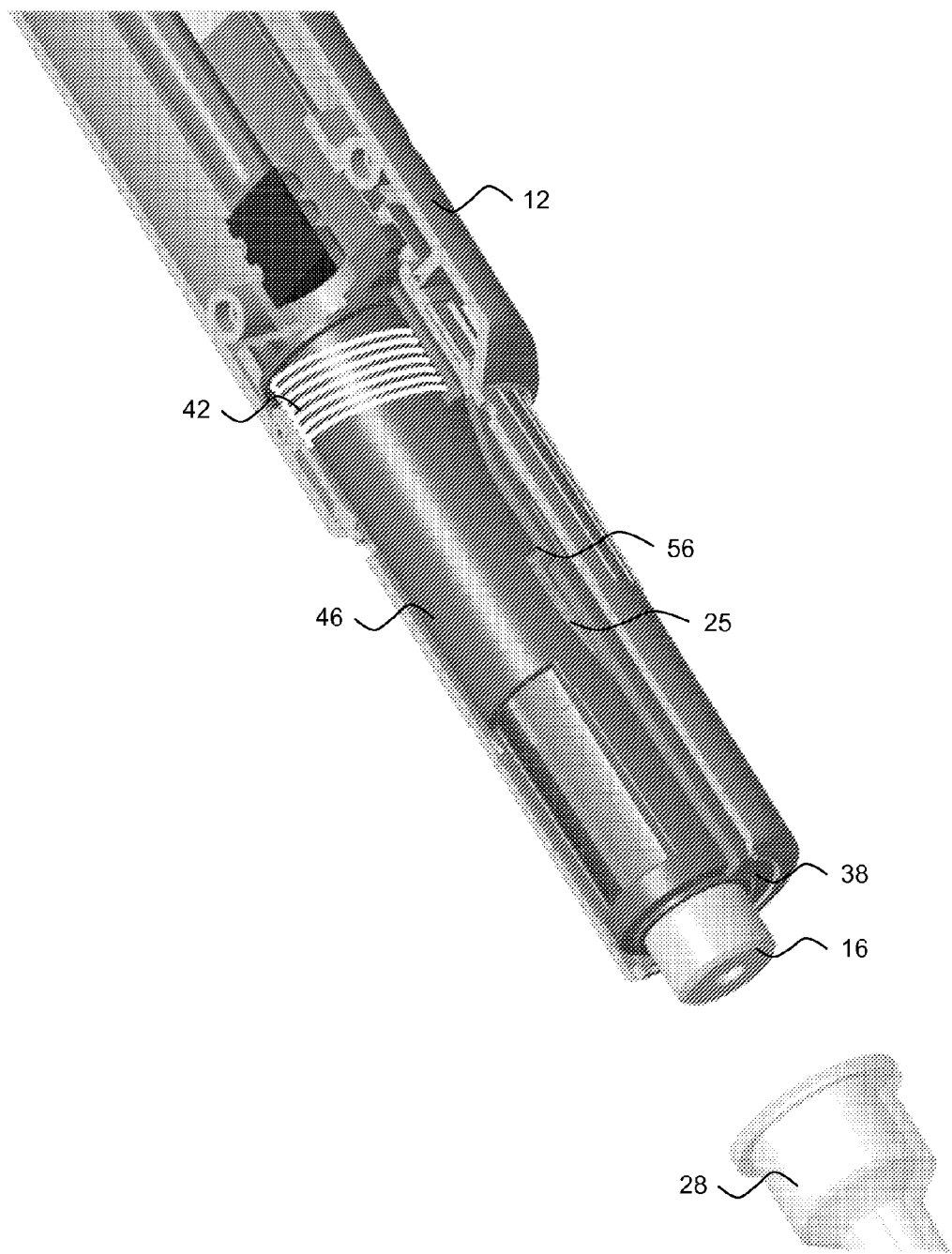
Figure 8:
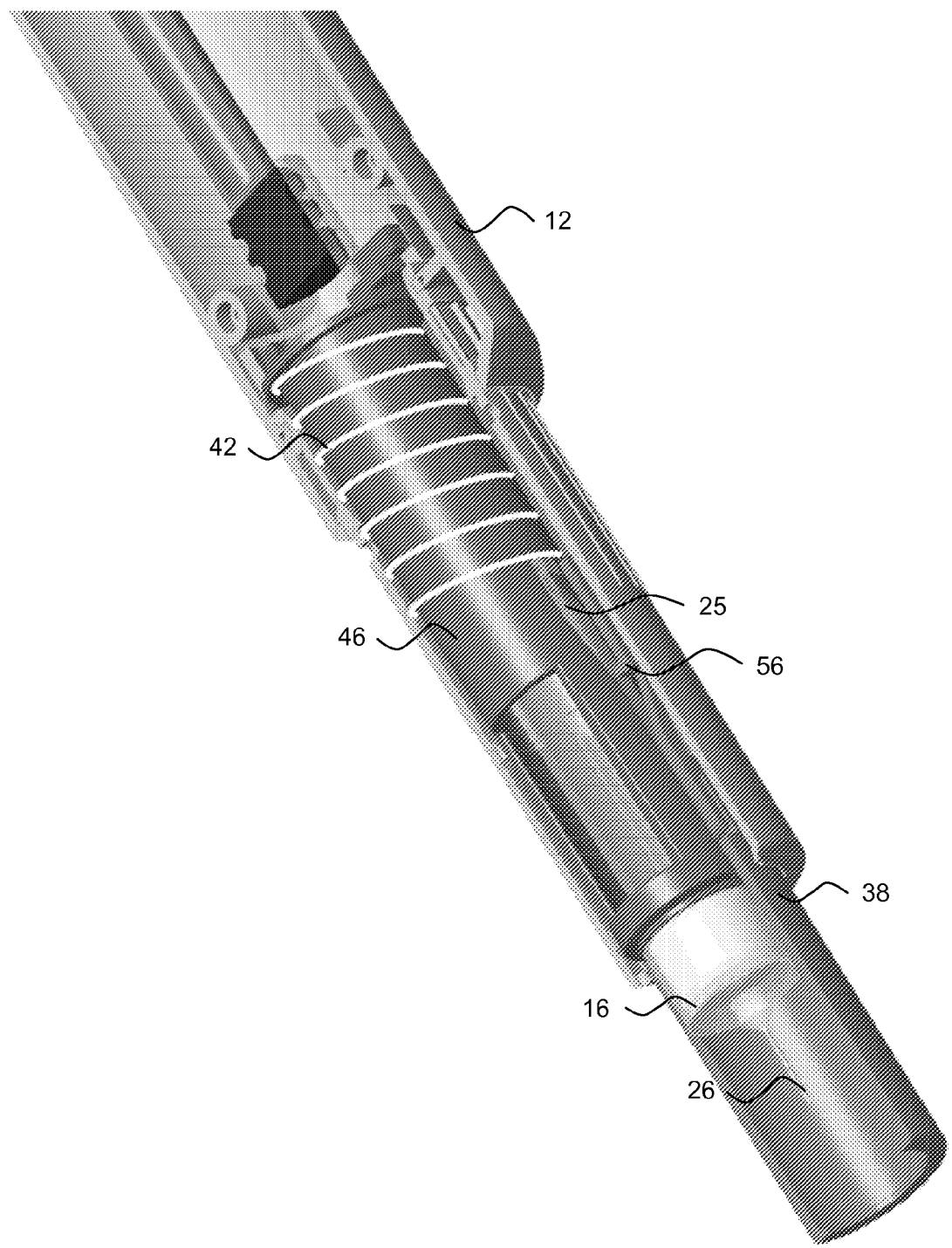
Figure 9:
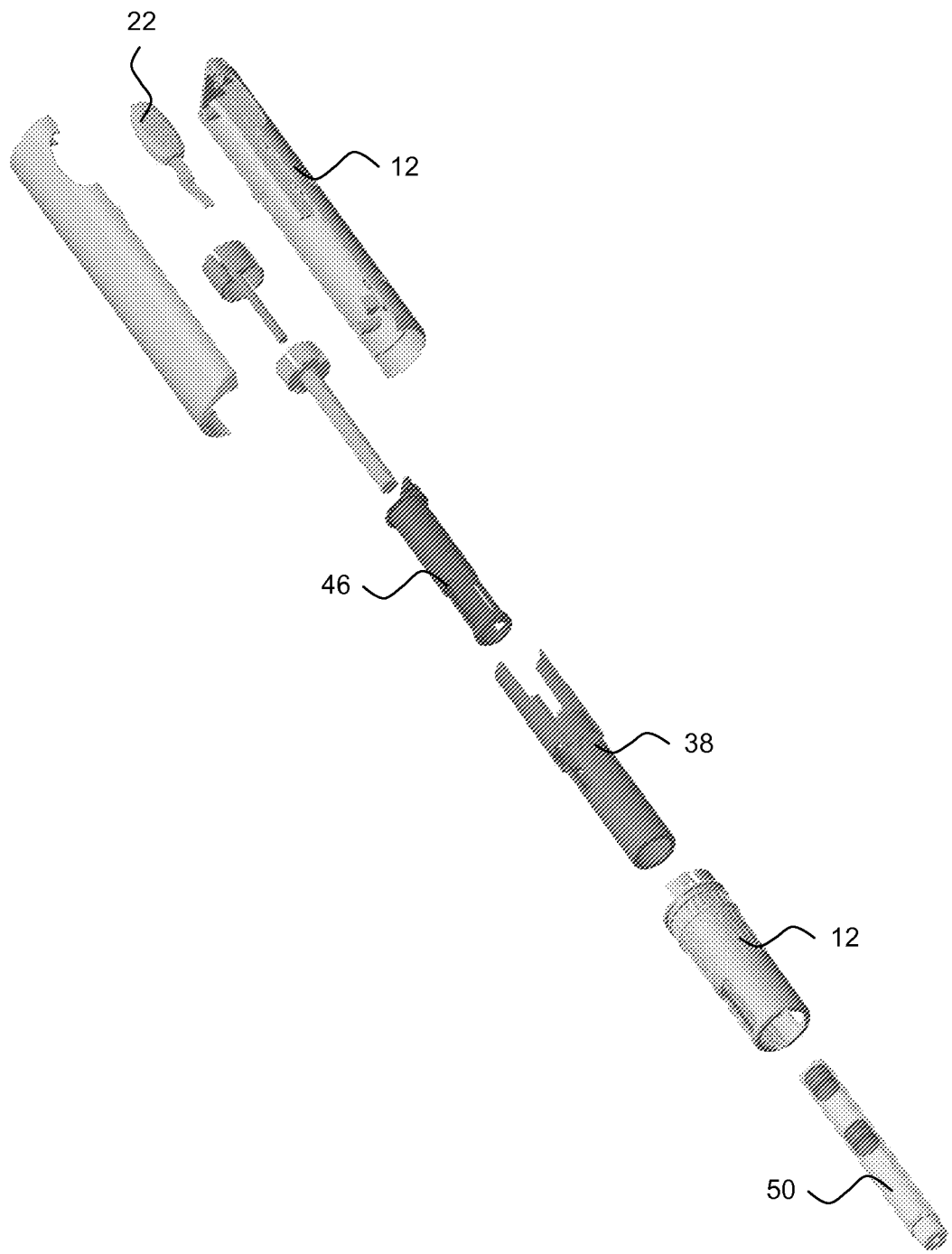
FIG. 9 shows in perspective and in an exploded view various important parts of the auto injector 10.
Figure 10:
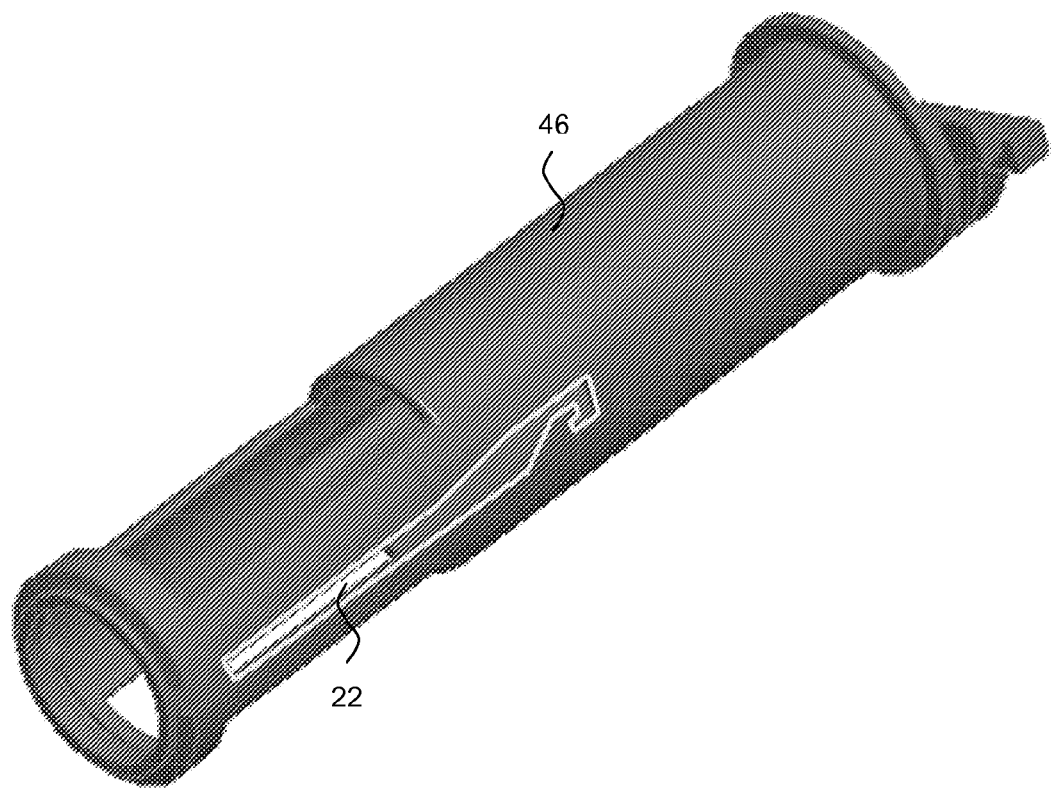
FIG. 10 shows the container housing 46 in more detail. The circumference of the slot 25 is marked with a white line.
Figure 12:
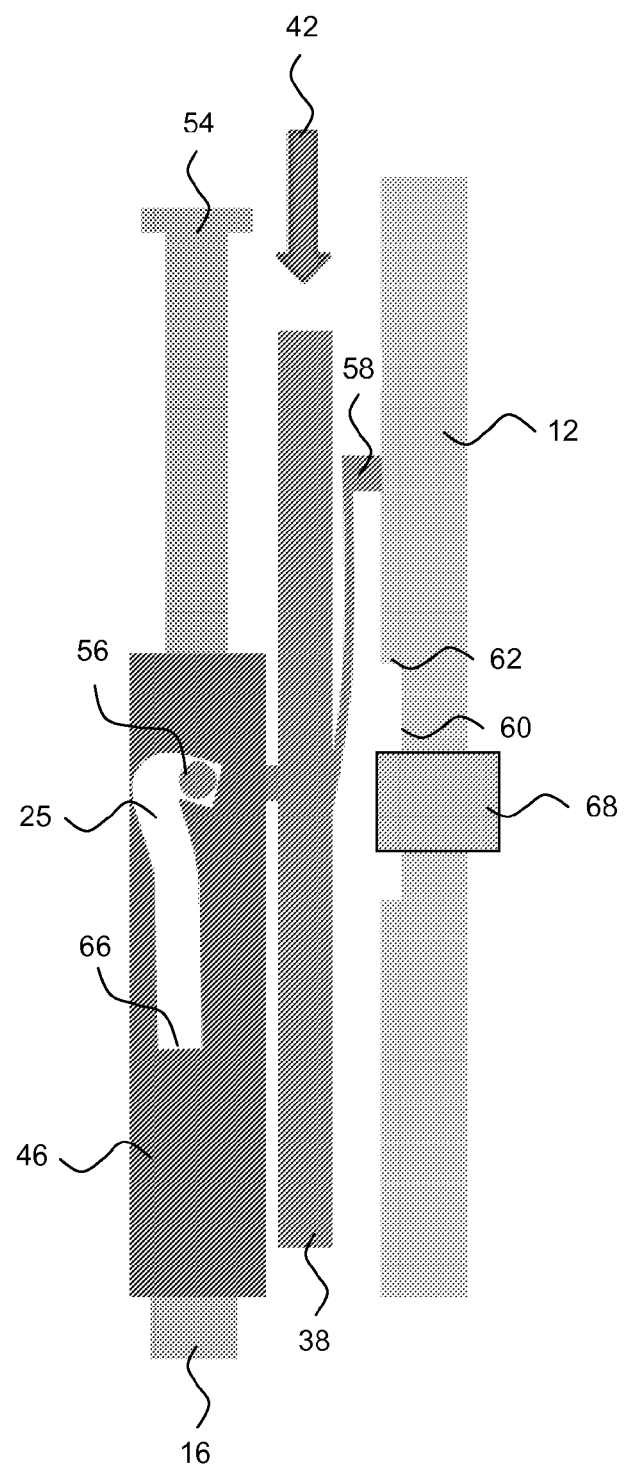

FIG. 12 shows an embodiment of the auto injector similar to the embodiment of FIGS. 4 and 5; with the difference that the tapered stop 64 in the groove 60 has been replaced by a movable member 68 that function as a mechanical stop both in the direction of forward movement of the needle shield 28 and rearward movement. The needle shield locking mechanism of the embodiment of FIG. 12 is identical to the locking mechanism shown in FIGS. 4 and 5. The needle shield 38 is coupled to a part of the housing 12, in the illustrated example the container housing 46, of the auto injector 10 with a locking mechanism like a bayonet lock. The locking mechanism prevents forward movement of the needle shield 38 in the direction towards the proximate end 14 of the auto injector 10 counteracting the force applied to the needle shield 14 by a needle shield driver 42 that moves the needle shield 38 forward upon release of the locking mechanism. The locking mechanism comprises an L-shaped slot 25 provided in the container housing 46 and a protrusion 56 of the needle shield 38 that cooperates with the slot 25. The protrusion 56 of the needle shield 38 fits in the slot 25 and engages with the slot 25 so that the slot 25 functions as a guiding rail for the protrusion 56. A short leg of the L-shaped part of the slot 25 spans circumferentially in the container housing 46 in a plane perpendicular to the longitudinal direction of the housing 12, and a long leg of the L-shaped part of the slot 25 spans in parallel with the longitudinal direction of the housing 12. In the retracted position of the needle shield 38 shown in FIG. 12, the protrusion 56 resides at the end of the slot 25 at the end of the short leg of the L-shaped slot 25 in which position, the protrusion 56 in cooperation with the slot 25 prevents forward movement of the needle shield 38 from its retracted position. The needle shield 38 is in a locked retracted position wherein the needle mounting site 16 is exposed to the surroundings for easy access during needle mounting.

The needle shield 38 further has a protrusion 58 that is resiliently connected to the needle shield 38 for cooperation with grooves 60 in the housing 12 for prevention of retraction of the needle shield 38 subsequent to forward movement of the needle shield 38 as will be further explained below.

When the needle 26 with the needle cap 28 is screwed onto the needle mounting site 16; during the final turn, the needle cap 28 engages with the container housing 46 and turns the container housing 46 a predetermined angle around the longitudinal axis of the housing 12, for example 45°, so that the protrusion 56 is moved to the opposite end of the short leg of the L-shaped slot 25 (by relative movement) and thereby to the start of the long leg of the L-shaped slot 25 whereby the needle shield 38 is released and allowed to move to its protruded position by the force applied by the needle shield driver (not shown). The slot 25 may be angled with relation to the longitudinal axis of the housing 12 so that the needle shield 38 is turned during part of the movement from the retracted position to the protruded position for re-alignment of other features of the needle shield, for example the distance piece explained below, with corresponding features in the housing facilitating subsequent operation of the auto injector 10.

Figure 13:
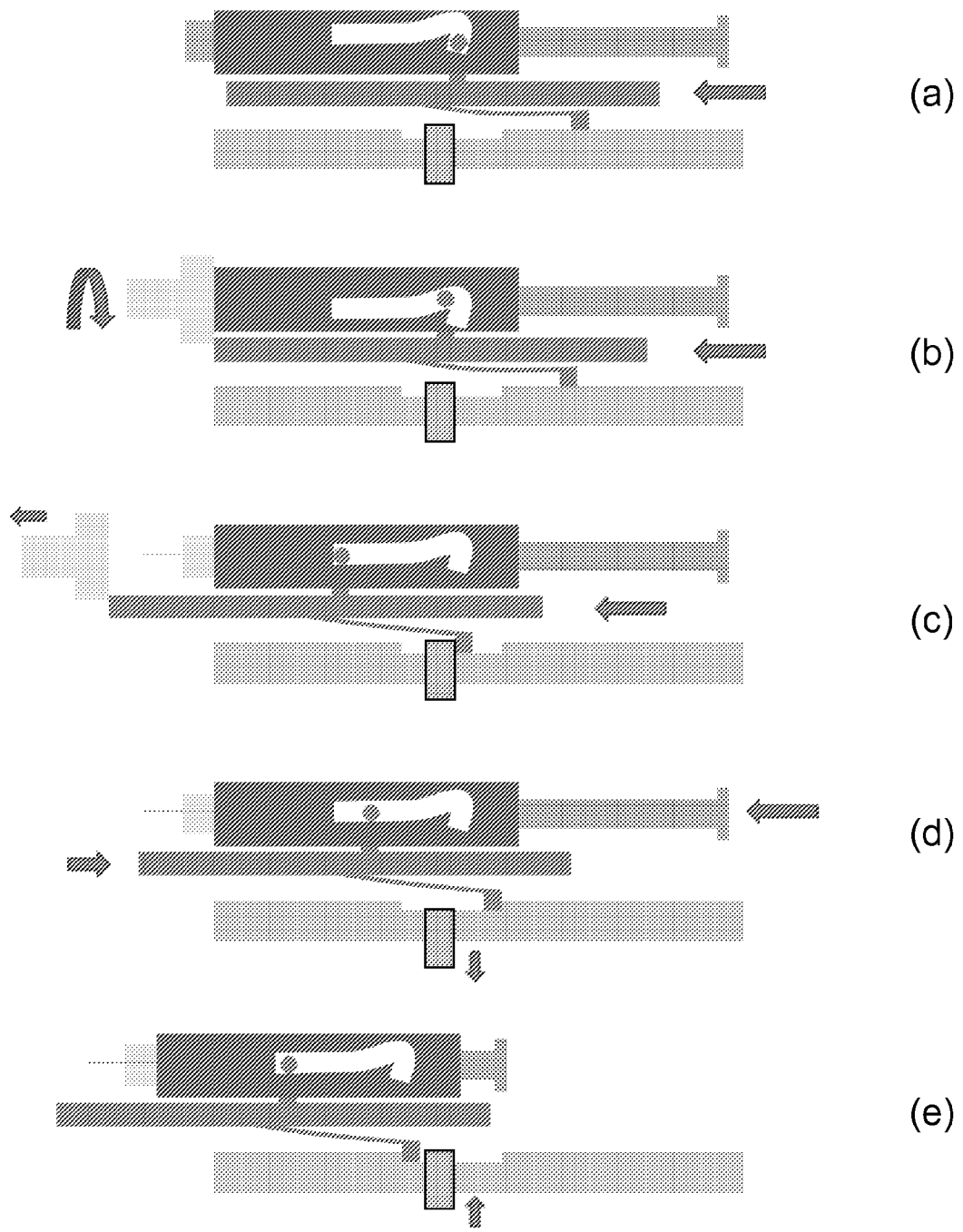

Various positions of the needle shield 38 are shown in FIG. 13 for illustration of various operational steps of the auto injector 10 in sequence from top to bottom of FIG. 13.

FIG. 13(*a*) shows the auto injector 10 before mounting of the needle as in FIG. 12.

In FIG. 13(*b*), the needle 26 has been mounted and the final turn of the needle cap 28 with the needle 26 has been performed whereby the needle shield 38 has been turned so that the protrusion 56 is now engaged with the long leg of the L-shaped slot 25 and is moved forward towards its protruded position by the needle shield driver 42, e.g. a coil spring, concurrently with user removal of the needle cap 28 from the needle 26. During removal of the needle cap 28, the needle cap 28 abuts the end of the needle shield 38 so that the needle shield 38 and the needle cap 28 moves forward in abutment whereby the needle 26 remains unexposed to the surroundings during mounting of the needle 26 and subsequent removal of the needle cap 28.

In FIG. 13(*c*), the needle shield 38 is in its first protruded position and the auto injector 10 is ready for injection. During forward movement of the needle shield 38, the protrusion 58 that is resiliently connected to the needle shield 38 slides along an internal wall of the housing 12 and is urged into the groove 60 in the wall by the spring force of the resilient interconnection with the needle shield 38. In the first protruded position, the protrusion 58 rests against the movable member 68.

In FIG. 13(*d*), the needle shield 38 is pressed against the injection site and injection is performed. The groove 60 cooperates with the protrusion 58 and has an end 62 that functions as a mechanical stop so that rearward movement of the needle shield 38 caused by pressing the needle shield against the injection site is stopped by abutment of the protrusion 58 and the end 62, whereby the injection site is not brought into contact with the needle 26 before user actuation of the auto injector 10 for injection. As illustrated in FIG. 13(*c*), the needle shield 38 is displaced rearward when the needle shield 38 is pressed against the injection site, whereby other features of the auto injector 10 are brought into relative positions that allow the user to trigger forward movement of the container housing 46 with the container 50 with the needle 26 for penetration of the injection site and injection of the medicament in the container compartment(s).

In FIG. 13(*e*), injection has been completed and the user has removed the auto injector 10 from the injection site. The forward movement of the container housing 46 has also moved the proximate end 66 of the slot 25 forward and the movable member 68 has been displaced to flush with the groove 60 so that the needle shield driver 42 is allowed to automatically move the needle shield 38 to its second protruded position upon removal of the auto injector 10 from the injection site. In its second protruded position, the needle shield 38 is fully protruded and locked by the tapered stop 64 provided in the groove 60. Upon passage of the displaced movable member 68 by the protrusion 58, the movable member 68 is moved back into its protruding position in the groove 60 where it prevents subsequent retraction of the needle shield 38 so that the needle 26 remains protected and covered by the needle shield after injection so that the auto injector 10 may be disposed safely, and further user contact with the needle 26 is prevented.

Figure 14:
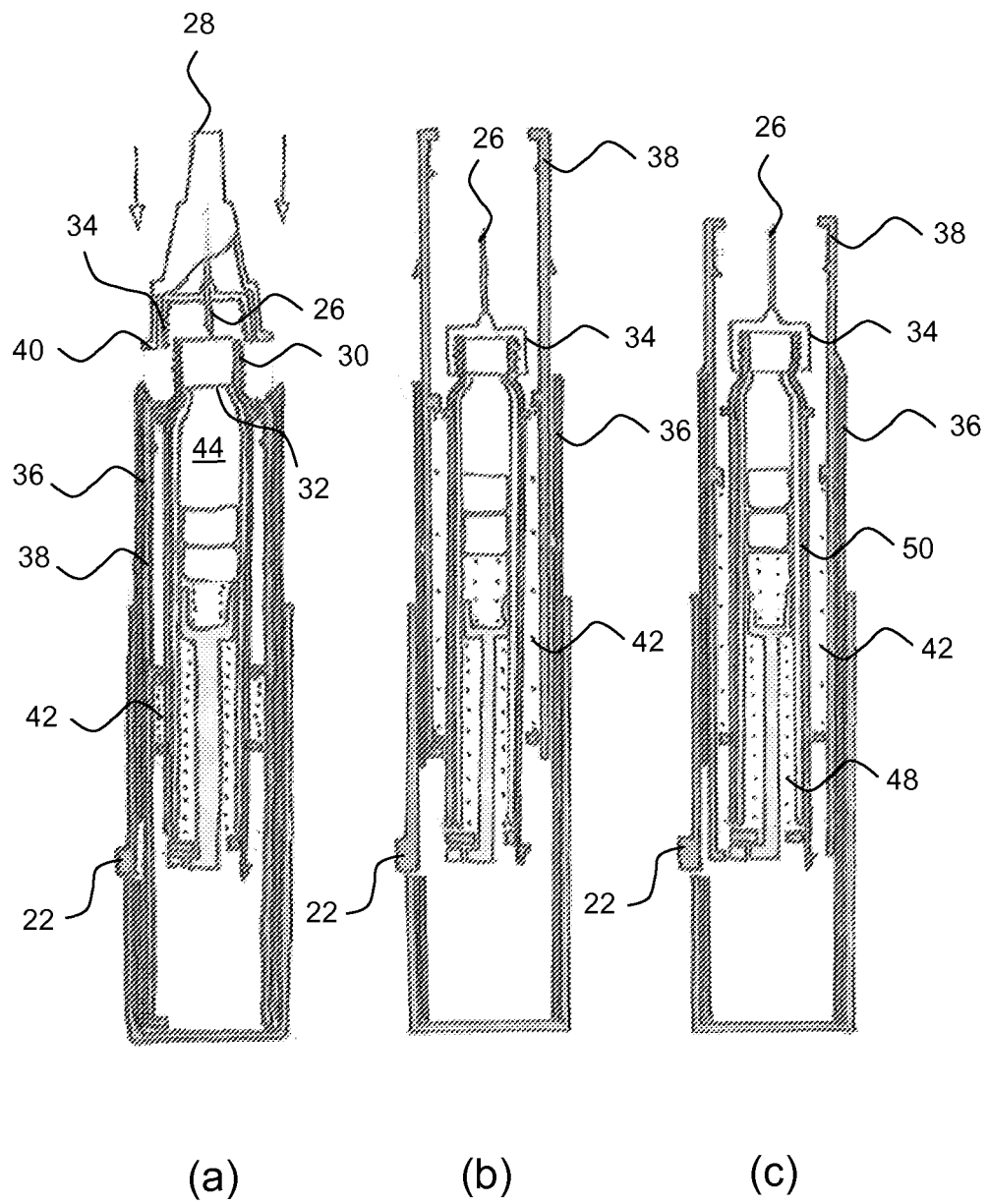

FIG. 14 schematically illustrates another embodiment of the invention. In FIG. 14, the needle mounting site 16 of the illustrated auto injector 10 comprises a cylindrical threaded member 30 with a central aperture covered by a seal 32. During mounting of the needle 26, the threaded cylindrical member 34 carrying the needle 26 is screwed onto the mating threaded member 30 of the needle mounting site 16 by the user gripping the needle cap 28. During the mounting operation, the needle 26 penetrates the seal 32 so that medicament in the auto injector may be delivered to the injection site through the needle 26. When the threaded cylindrical member 34 carrying the needle 26 has been screwed fully, or substantially fully, onto the mating threaded cylindrical member 30 thereby connecting the needle sealingly with the interior of the auto injector 10, needle shield locking arms 36 holding the needle shield 38 of the auto injector 10 in a retracted position inside the auto injector are automatically released by interaction with protrusions 40 of the needle cap 28 so that the needle shield driver 42, in the illustrated example, a coil spring 42, urges the needle shield 38 out of the auto injector concurrent with user removal of the needle cap 28 from the threaded member 34 holding the needle 26. FIG. 4(b) shows the needle shield 38 in a protruded position wherein the auto injector 10 is ready for further operation, i.e. mixing in the event that mixing is necessary and automatic injection at the injection site possibly preceded by priming. Until proper mounting of the needle, further operation of the auto injector 10 is not possible. The auto injector 10 is locked until the needle 26 has been properly mounted to the mounting site 16 and the needle shield 38 has been moved forward to its protruded position.

In order to continue operation after proper mounting of the needle 26, the turning knob 18 may be rotated further to initiate a possible mixing step in the event that the medicament requires mixing and possible priming. The container 50 may for example have two chambers, wherein one chamber may contain freeze-dried medicine and the other chamber may contain liquid to be mixed with the freeze-dried medicine.

During priming, possible excess air in the compartment 44 holding medicament is ejected through the needle.

In another auto injector in which needle mounting is performed after mixing of the medicament, priming may be automatically performed upon needle mounting driven by excess pressure in the chamber with the medicament. The excess pressure drives excess air and possibly a portion of the mixed medicament out of the chamber through the needle.

In the illustrated auto injector 10, the priming process is manually controlled by the user subsequent to needle mounting and mixing. The user stops the priming when the first amount of medicament appears at the needle tip as inspected through the large opening in the sides of the needle shield.

For some types of medicament, it is not necessary to perform priming.

When ready for injection, the auto injector 10 is moved to the injection site, and the needle shield 38 is pressed against the injection site and into a retracted position in which the needle is still accommodated behind the needle shield out of contact with the injection site as schematically shown in FIG. 14(c). This releases the second injection lock by establishing a connection between the injection trigger member 22 and the first injection lock in such a way that pressing the injection trigger member 22 inside the housing 12 of the auto injector 10 leads to release of the first injection lock.

When the first injection lock has been released, the injection driver 48 moves the container 50 together with the needle 26 from its current first position, in which position the needle 26 is accommodated behind the needle shield 38, to its second position, in which position the needle 26 protrudes beyond the needle shield 38, and penetrates tissue of the injection site. The injection driver 48 then moves the piston 52 further into the container compartment 44 and forces the medicament in the compartment 44 out through the needle 26.

In the illustrated auto injector 10, release of the injection trigger member 22 after commencement of injection and before completion of the injection causes medicament injection to stop, and subsequent actuation of the injection trigger member 22 causes medicament injection to be resumed.

Likewise, release of the needle shield 38 after commencement of injection and before completion of the injection causes medicament injection to stop, and subsequent pressing the needle shield 38 against the injection site causes medicament injection to be resumed.

Figure 15:
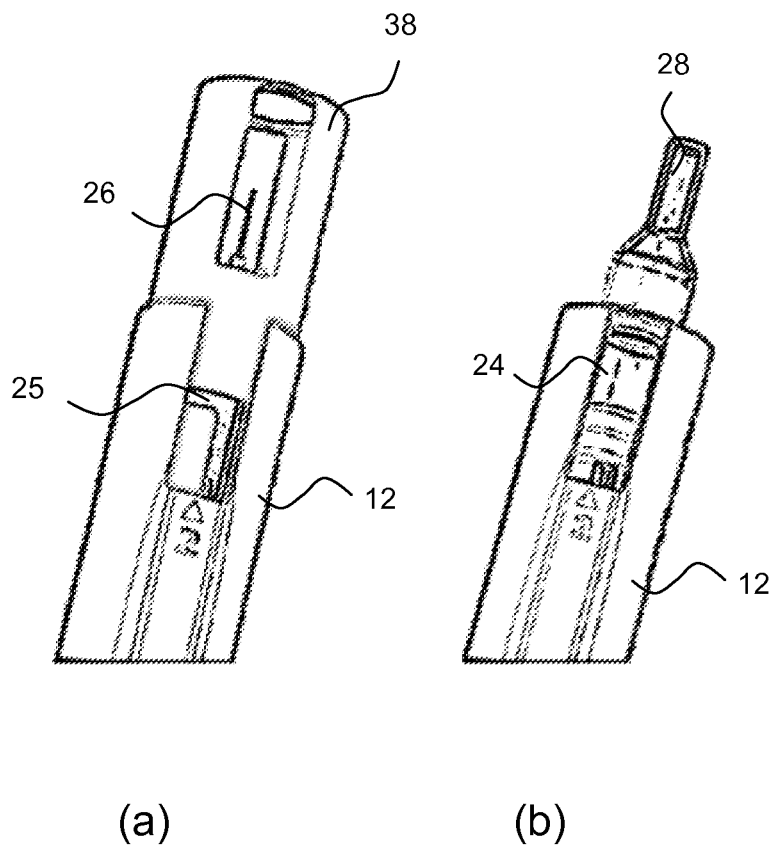

FIG. 15 schematically illustrates another release mechanism for the needle shield 38 wherein the needle shield 38 is coupled to the housing 12 of the auto injector with a bayonet lock. An L-shaped part of a slot 25 in the needle shield 38 is visible in FIG. 5(a) and forms part of the bayonet lock. A short leg of the L-shaped part of the slot 25 extends circumferentially in the needle shield 38 in a plane perpendicular to the longitudinal extension of the housing 12, and a long leg of the L-shaped part of the slot 25 extends in parallel with the longitudinal extension of the housing. A protrusion (not visible) inside the housing engages with the slot and in the retracted position of the needle shield 38 shown in FIG. 15(b), the protrusion resides at the end of the slot at the end of the short leg of the L-shaped part of the slot 25 in which position, the protrusion prevents movement of the needle shield 38 from its retracted position shown in FIG. 15(b) to a protruded position shown in FIG. 15(a). When the needle 26 with the needle cap 28 is screwed onto the needle mounting site, the needle cap 28 engages with the needle shield 38 and turns the needle shield a predetermined angle around the longitudinal axis of the housing, for example 45°, so that the protrusion is moved to the end of the long leg of the L-shaped part of the slot 25 (by relative movement) whereby the needle shield 38 is released and allowed to move to the protruded position of FIG. 15(a). The slot 25 may be angled (not visible) with relation to the longitudinal axis of the housing 12 so that the needle shield 38 is turned during part of the movement from the retracted position to the protruded position for re-alignment of other features of the needle shield, for example the distance piece explained below, with corresponding features in the housing facilitating subsequent operation of the auto injector.

Figure 16:
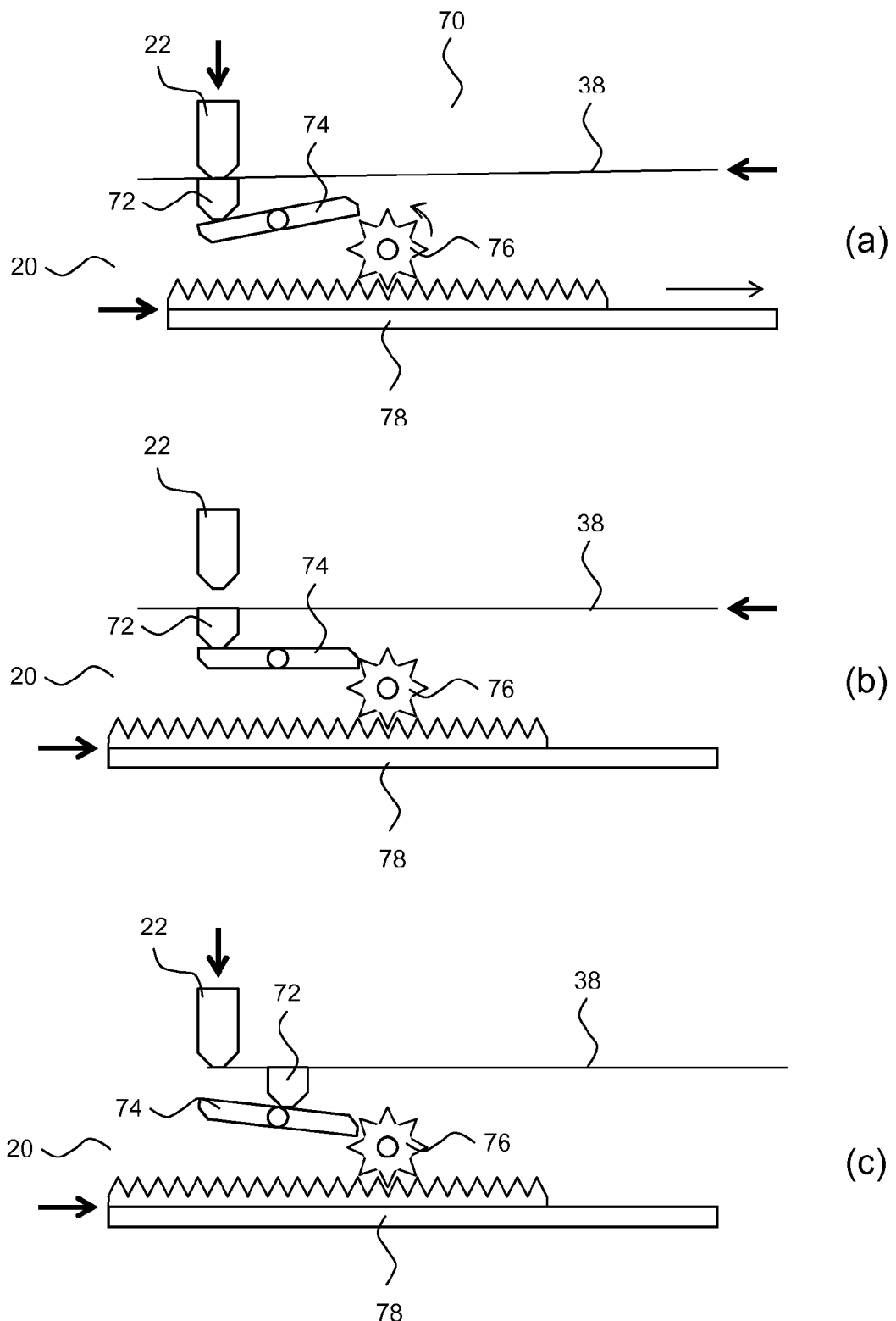

FIG. 16 schematically illustrates part of an injection mechanism 70 that allows the user to stop and restart injection for example to relieve possible pain felt during the injection process.

In FIG. 16(a), the injection trigger member 22 is pressed by the user and the needle shield 38 (only a part of the needle shield is visible) is pressed against the injection site (not shown) so that a distance piece 72 is positioned between the injection trigger member 22 and a pivotable bar 74. When pressed, the injection trigger member 22 in cooperation with the distance member 72 turns the pivotable bar 74 out of engagement with the toothed wheel 76 whereby the toothed wheel 76 is allowed to rotate freely which in turn allows the toothed rack 78 driven by the injection driver 48 (not shown) to move the piston (not shown) further into the chamber (not shown) with the medicament thereby performing the injection.

In FIG. 16(b), the injection trigger member 22 is released by the user whereby the distance piece 72 is also released and as a result the pivotable bar is turned into engagement with the toothed wheel 76 thereby locking the toothed wheel 76 and preventing the rack 78 from moving the piston and thus, injection is stopped. In the event that injection has not been completed, injection may be resumed by reverting to the situation illustrated in FIG. 16(*a*) wherein the needle shield 38 is pressed against the injection site and the injection trigger member 22 is also pressed.

In FIG. 16(*c*), the needle shield 38 is released from the injection site so that the distance piece 72 is moved away from the position in which it cooperates with the injection trigger member 22 to allow continued injection. Instead, the distance piece 72 is moved to a position in which it keeps the pivotable bar 74 in engagement with the toothed wheel 76 whereby the toothed rack 78 is locked and the injection is stopped. In the event that injection has not been completed, injection may be resumed by reverting to the situation illustrated in FIG. 16(*a*) wherein the needle shield 38 is pressed against the injection site and the injection trigger member 22 is also pressed.

The invention claimed is:

1. An auto injector comprising:
a housing for accomodation of:
a container with at least one compartment for accommodation of a medicament to be injected,
a needle mounting site for user mounting of a needle covered by a removable needle cap,
a needle shield that is accommodated in the housing and that is movable along a longitudinal axis of the housing with relation to a fixed part of the housing,
a needle shield driver that is anchored to the fixed part of the housing and connected to the needle shield for displacing the needle shield along the longitudinal axis of the housing with relation to the fixed part of the housing, and
a needle shield locking mechanism that keeps the needle shield in a retracted position before mounting of the needle wherein the needle shield locking mechanism is released during mounting of the needle with the needle cap to the needle mounting site whereby the needle shield driver, upon release of the needle shield locking mechanism and concurrently with user removal of the needle cap from the needle, displaces the needle shield from its retracted position to a first protruded position in which the needle shield prevents inadvertent user contact with the needle.

2. An auto injector according to claim 1, further comprising a container housing for accommodation of the container, and wherein the locking mechanism comprises an L-shaped slot provided in a wall in the container housing and a first protrusion of the needle shield that is movably accommodated in the slot and wherein the L-shaped slot has an orientation that prevents movement of the needle shield with the first protrusion along the longitudinal axis of the housing before mounting of the needle and wherein the locking mechanism is released when the wall is turned by the needle cap during mounting of the needle by abutment of the wall and the needle cap whereby the first protrusion is moved in the L-shaped slot to a position where the L-shaped slot changes direction and allows the needle shield with the first protrusion to be displaced along the longitudinal axis of the auto injector by the force of the needle shield driver.

3. An auto injector according to claim 1, wherein the locking mechanism comprises an L-shaped slot provided in the needle shield and a first protrusion of a wall in the housing that is movably accommodated in the slot and wherein the L-shaped slot has an orientation that prevents movement of the needle shield with relation to the first protrusion along the longitudinal axis of the housing before mounting of the needle and wherein the locking mechanism is released when the needle shield is turned by the needle cap during mounting of the needle by abutment of the needle shield and the needle cap whereby the first protrusion is moved in the L-shaped slot to a position where the L-shaped slot changes direction and allows the needle shield to be displaced with relation to the first protrusion along the longitudinal axis of the auto injector by the force of the needle shield driver.

4. An auto injector according to claim 1, wherein the locking mechanism comprises a needle shield locking arm of the housing, having a protrusion that engages and holds a proximate end of the needle shield at the needle mounting site thereby keeping the needle shield of the auto injector in the retracted position before mounting of the needle, and wherein the locking mechanism is released when a protrusion of the needle cap displaces the protrusion of the needle shield locking arm out of engagement with the needle shield during mounting of the needle and allows the needle shield to be displaced with relation to the fixed part of the housing along the longitudinal axis of the auto injector by the force of the needle shield driver.

5. An auto injector according to claim 1, wherein the needle shield is pressed into a retracted position defined by a mechanical stop provided in the housing when the needle shield is pressed against an injection site in which retracted position the needle shield prevents the needle from contacting the injection site, and in which retracted position the needle shield establishes a connection between an injection trigger member provided in the housing and a first injection lock in such a way that pressing the injection trigger member releases the first injection lock whereby an injection driver moves the container together with the needle from its current first position, in which position the needle is accommodated behind the needle shield, to a second position, in which position the needle protrudes beyond the needle shield for penetration of tissue at the injection site.

6. An auto injector according to claim 5, wherein release of the injection trigger member after commencement of injection and before completion of the injection stops medicament injection, and subsequent actuation of the injection trigger member resumes medicament injection.

7. An auto injector according to claim 5, wherein release of the needle shield after commencement of injection and before completion of the injection stops medicament injection, and subsequent pressing the needle shield against the injection site resumes medicament injection.

8. An auto injector according to claim 1, wherein the needle shield has a second protrusion that is resiliently connected to the needle shield and configured to slide along an internal surface of the housing when the needle shield is displaced along the longitudinal axis of the auto injector and urged into abutting contact with the surface by the spring force of the resilient connection to the needle shield.

9. An auto injector according to claim 8, wherein a groove is provided in the internal surface of the housing, the groove having a longitudinal direction that is parallel to the longitudinal axis of the housing and that accommodates the second protrusion urged into the groove by the spring force of the resilient interconnection with the needle shield when the needle shield is in the first protruded position.

10. An auto injector according to claim 9, wherein the groove has a distal end defined by an end wall of the groove that functions as a mechanical stop so that rearward movement of the needle shield caused by pressing the needle shield against the injection site is stopped by abutment of the second protrusion and the distal end of the groove.

11. An auto injector according to claim 10, further comprising a tapered protrusion in the groove that allows passage of the second protrusion in the forward moving direction of the needle shield and prevents passage of the second protrusion in the rearward moving direction of the needle shield so that the needle shield is allowed to move to a second protruded position upon removal of the auto injector from the injection site upon completion of an injection and prevents subsequent retraction of the needle shield from the second position by abutment of the second protrusion and the protrusion so that the needle remains protected and covered by the needle shield after injection.

12. An auto injector according to claim 10, further comprising a movable member in the groove that defines the first protruded position of the needle shield by abutment of the second protrusion and the movable member and that is displaced out of abutment with the second protrusion thereby allowing passage of the second protrusion in the forward moving direction of the needle shield so that the needle shield is allowed to move to a second protruded position upon removal of the auto injector from the injection site upon completion of an injection and that is returned into its protruding position in the groove upon passage of the second protrusion in the forward moving direction of the needle shield and prevents passage of the second protrusion in the rearward moving direction of the needle shield thereby preventing subsequent retraction of the needle shield from the second position by abutment of the second protrusion and the movable member so that the needle remains protected and covered by the needle shield after injection.

13. An auto injector according to any of the previous claims, wherein the needle mounting site is accommodated in the housing in a retracted and inaccessible position before mounting of the needle and wherein the needle mounting site is further configured to be moved forward to an accessible position for mounting of the needle by a mounting site driver upon user actuation of the auto injector.

14. An auto injector according to any of the previous claims, wherein the auto injector is prevented from further operation until proper mounting of the needle.

* * * * *